US008047069B2

(12) United States Patent
Coulter et al.

(10) Patent No.: US 8,047,069 B2
(45) Date of Patent: Nov. 1, 2011

(54) APPARATUS FOR DETERMINING CUT RESISTANCE

(75) Inventors: William Herbert Coulter, Wilmington, DE (US); Mark Allan Lamontia, Landenberg, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 30 days.

(21) Appl. No.: 12/787,445

(22) Filed: May 26, 2010

(65) Prior Publication Data

US 2010/0300195 A1 Dec. 2, 2010

Related U.S. Application Data

(60) Provisional application No. 61/181,027, filed on May 26, 2009.

(51) Int. Cl.
*G01L 5/04* (2006.01)
(52) U.S. Cl. ......................................................... 73/159
(58) Field of Classification Search .................... 73/159, 73/760, 104, 788
See application file for complete search history.

(56) References Cited

U.S. PATENT DOCUMENTS

| 2,436,435 | A | * | 2/1948 | Kent | 73/85 |
| 3,817,090 | A | * | 6/1974 | Michel | 73/81 |
| 3,827,281 | A | * | 8/1974 | Hamel | 73/7 |
| 4,864,852 | A | | 9/1989 | Boone | |
| 5,333,494 | A | * | 8/1994 | Kishima et al. | 73/104 |
| 5,613,414 | A | | 3/1997 | Murphy et al. | |
| 6,681,622 | B1 | * | 1/2004 | Valentine et al. | 73/159 |
| 7,121,136 | B2 | * | 10/2006 | Tsujii et al. | 73/81 |
| 7,320,242 | B2 | * | 1/2008 | Hoo Fatt et al. | 73/12.14 |
| 7,694,964 | B2 | * | 4/2010 | Kawasaki et al. | 271/263 |
| 2008/0073020 | A1 | * | 3/2008 | Lammlein | 156/110.1 |
| 2010/0018298 | A1 | * | 1/2010 | Kanematsu et al. | 73/104 |

* cited by examiner

*Primary Examiner* — Lisa Caputo
*Assistant Examiner* — Jamel Williams

(57) ABSTRACT

An apparatus and a method of using the apparatus for measuring the cut resistance of polymeric and elastomeric materials having specimen holding and tensioning devices arranged on a common axis; a blade cutting device located orthogonally to the axis of the first and second specimen tensioning devices and a cutting block assembly located on the same axis as the cutting device and on the opposite side of the specimen tensioning device.

2 Claims, 2 Drawing Sheets

APPARATUS FOR DETERMINING CUT RESISTANCE

BACKGROUND OF THE INVENTION

1. Field of the Invention

This invention relates to an apparatus for determining the cut resistance of materials under tension 2. Description of the Related Art U.S. Pat. No. 5,613,414 describes a device that employs a heated knife for cutting elastomeric materials such as those used for tire treads. US patent Publication 2008/0073020 describes an apparatus and method for cutting elastomeric components in the tire building process. U.S. Pat. No. 4,864,852 describes an apparatus and method to cut flexible materials used in protective apparel. However, these references do not address the need for an apparatus and method for testing the cut resistance of automobile tire sidewalls that are in tension as a result of tire inflation pressure.

DETAILED DESCRIPTION OF THE INVENTION

Figure 1:
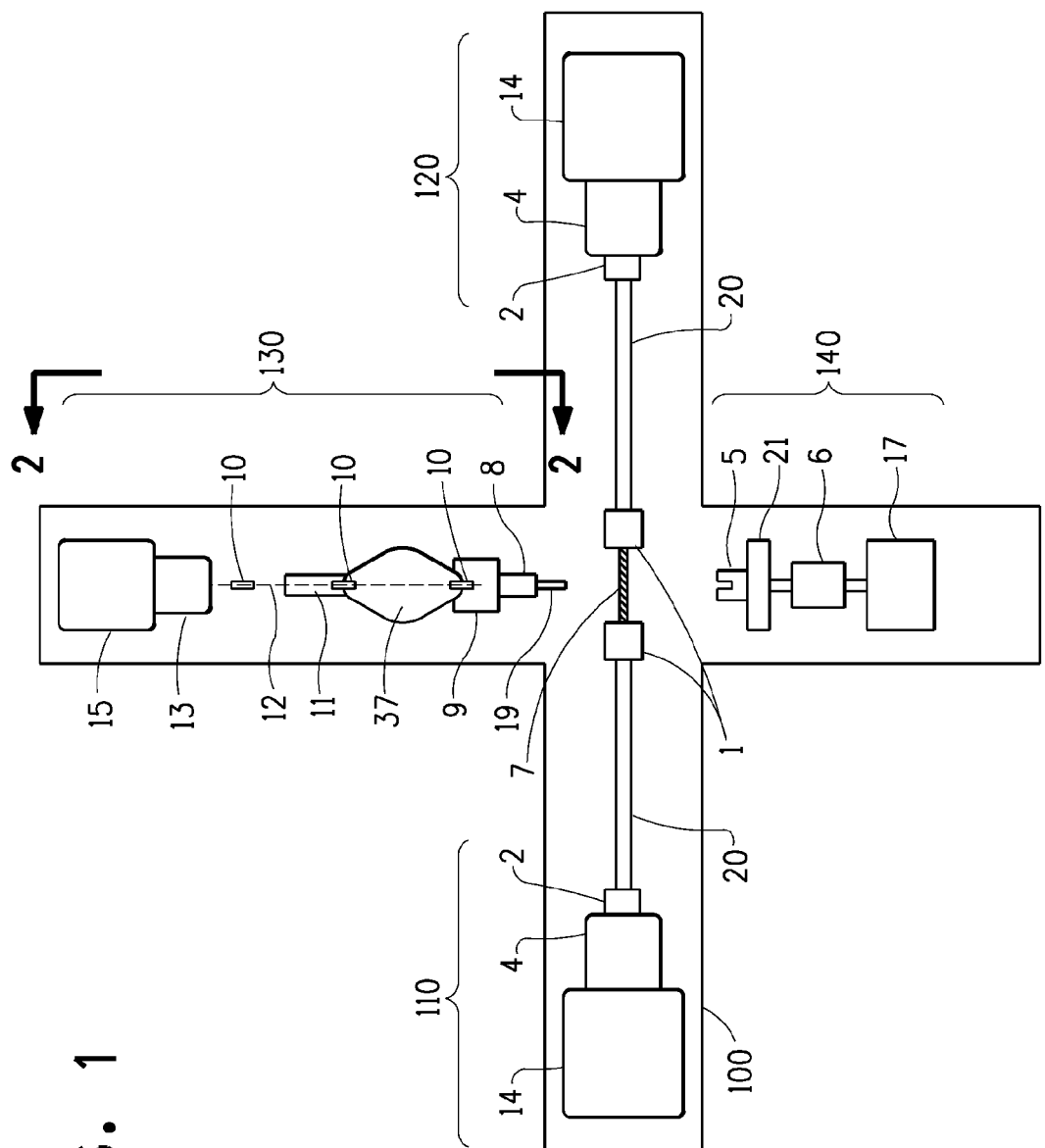
FIG. 1 is an overall-view of the testing machine.

This invention is directed to an apparatus and method of using the apparatus for measuring the cut resistance of polymeric and elastomeric materials under conditions that closely simulate those found in field use. As an example, automobile tire sidewalls are in tension as a result of tire inflation pressure. The apparatus described herein permits elastomeric specimens representing the sidewall to be cut while under tension that simulates an inflated tire. The apparatus comprises with respect to FIGS. 1 and 2

(a) first and second specimen holding and tensioning devices 110 and 120 arranged on a common axis wherein the tensioning devices each comprise an assembly of components connected together in the sequential order of test specimen grips 1, connecting rods 20, release couplings 2, load cells 4 and actuators 14, (b) a cutting device 130 located orthogonally to the axis of the first and second specimen tensioning devices wherein the cutting device further comprises a cutting blade 19, a blade holder 8 on a linear slide 9 supported by a knee 11, a load cell 13 and wherein the blade holder is connected to the load cell via a wire 12 that extends over a plurality of pulleys 10, and (c) a cutting block assembly 140 located on the same axis as the cutting device and on the side of the specimen tensioning device axis opposite the cutting device, wherein the cutting block assembly is comprised of components connected together in the sequential order of cutting block 5, air cylinder 21, load cell 6 and an actuator 17, wherein the cutting block further comprises a first slot 28 cut horizontally across the block to locate the test specimen and a second slot 29 cut vertically to locate the cutting blade. The apparatus may be mounted on support base 100 that insulates the apparatus from the floor and provides channels (not shown) for the movement of the various components of the apparatus along their respective axes.

As shown in FIG. 1, a test specimen 7 is held in place with two grips 1. Preferably, the grips are mechanical. The grips are attached to load cells 4 with threaded rods 20 and quick release couplings 2. The grips 1 and rods 20 are supported to minimize any moment induced on load cells 4 by the weight of the grip assembly The quick release couplings allow the user to quickly replace test specimens. The couplings also are designed to pivot while the test specimen is being cut, assuring the cutting block presses the sample against the blade with a constant force throughout the test.

Load cells 4 are used to monitor and maintain specimen tension. The load cells are mounted to actuators (linear motors) 14. In each instance when actuators are referred to herein, it is understood that linear displacement transducers (not shown) are mounted internally within the actuators and are used to monitor actuator travel along the respective axes. Further, in each instance when actuators are referred to herein it is preferable that hydraulic actuators are used.

FIG. 1 also shows a blade 19 held in a blade holder 8. One example of a suitable blade is a double bevel razor blade. The blade holder is designed to align and position the blade 19 the same way for each test. Further, the blade holder can be modified as needed to accept blades with different shapes and lengths. The blade holder 8 is attached to a vertically mounted low friction linear slide 9. This linear slide is supported by a knee 11. Attached to the top of the blade holder, directly along the centerline of the blade, is wire 12. The wire is directed through a series of pulleys 10 to an attachment point on a load cell 13. The wire can be made of metal, plastic or any material of sufficient strength and durability suitable for use in such an application. The load cell is rigidly mounted to an actuator 15. By using the series of pulleys shown in FIG. 1 the horizontal motion of the actuator 15 can be translated into vertical motion of blade 19. Although three pulleys (two shown as supported by plate 37) are shown in FIG. 1, any number can be used as long as the horizontal motion of the actuator is appropriately translated into vertical motion of the blade. The load cell 13 is used to monitor load required to pull the blade through the specimen as it is being cut. The arrangement of certain of the features of the subject apparatus are depicted in a side view in FIG. 2.

A cutting block 5 is used to press the test specimen 7 against the blade 19 and hold the specimen in place as the blade cuts through the specimen. The cutting block is mounted directly to air cylinder 21. The air cylinder is attached to a load cell 6 which is rigidly mounted to an actuator 17. The load cell 6 is used to monitor and control the force with which the test specimen is pressed against the blade 9. Linear displacement transducers (mounted internally within the actuator) are used to monitor the cutting block travel and detect when the cutting block 5 is in contact with the blade 19.

The air cylinder 21 acts as a mechanical fuse to protect the load cell 6. After the test specimen is cut it is possible for the blade 19 to impact the cutting block 5, thereby generating large forces which could damage the load cell 6. To protect against this, the air cylinder 21 is mounted in series between the cutting block 5 and the load cell 6. Air cylinder 21 is connected to a pressurized air source (not shown) and is controlled using a regulator. The required pressure selected to assure the force required to move the air cylinder is approximately 90% of the maximum rating of load cell 6. This assures the cylinder will not affect normal testing, but still protect the load cell, as needed.

The motion of the actuators can be controlled by a PC based controller (not shown). The signals from the load cells as well as the linear transducers monitoring the actuators go directly to the PC controller. Actuators 14 apply and maintain tension to test specimen 7 during the test. The signals from load cells 4 are averaged together and the PC controller continuously adjusts the position of actuators 14 to maintain the desired load while keeping test specimen 7 centered within the cutting block. The tension level is controlled by adjusting a setting within the PC controller software. Actuator 17 is used to press test specimen 7 against blade 19 with a specified load. The signal from load cell 6 is monitored and the position of actuator 17 is continuously adjusted to maintain the specified load. The amount of force used to push test specimen 7 against blade 19 is adjusted with a setting within the PC controller. Actuator 15 is used to draw the blade 19 across test specimen 7 until it is cut or the entire length of blade has traveled across the specimen. The PC controller moves actuator 15 at a specified rate, which can be adjusted within the PC controller software. The test ends when any one of three conditions is satisfied: (1) if the PC controller detects that actuator 15 has traveled a distance equal to the length of blade 19 the test will stop, (2) if the PC controller detects the tension applied to test specimen 7 drops to zero, while trying to adjust the position of actuators 14 to increase tension, the test will stop and (3) if the PC controller detects that cutting block 5 contacts blade 19, either by the position of actuator 17 or from a sudden increase in load sensed by the load cell 6, the test will stop. Following the test the PC controller will re-set all actuators in preparation for another test.

Figure 3:
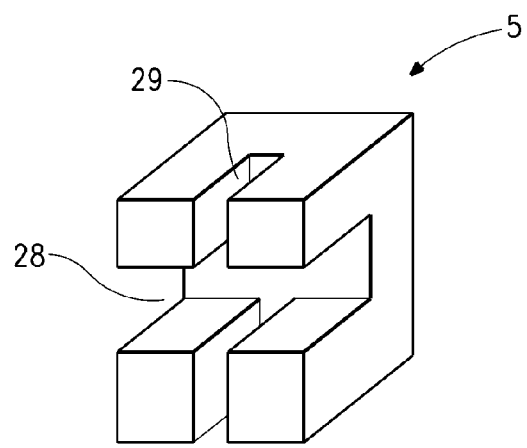
FIG. 3 is a view of a cutting block against which the specimen is cut.

FIG. 3 depicts cutting block 5, against which the specimen is cut. The block can be made from a polymeric material with a Rockwell hardness of no greater than 120 R and a low friction coefficient. Suitable materials for the cutting block include nylon 6,6 and polyoxymethylene. Using a polymeric material instead of a metallic material dampens the loads produced when the cutting block is driven into the blade by the actuator 17 after the test specimen has been successfully cut. There are two mutually perpendicular slots in the cutting block. The horizontal slot 28 positions the specimen and assures it will not move as the blade travels across the surface of the specimen. The width of the horizontal slot is preferably slightly larger than the width of the test specimen and the depth of the slot is preferably slightly less than the exposed portion of blade when installed in the blade holder. The vertical slot 29 allows the blade to travel and penetrate the test specimen. The width of the vertical slot is preferably slightly greater than twice the thickness of the blade. The vertical slot is machined to the same depth as the horizontal slot previously described.

Figure 2:
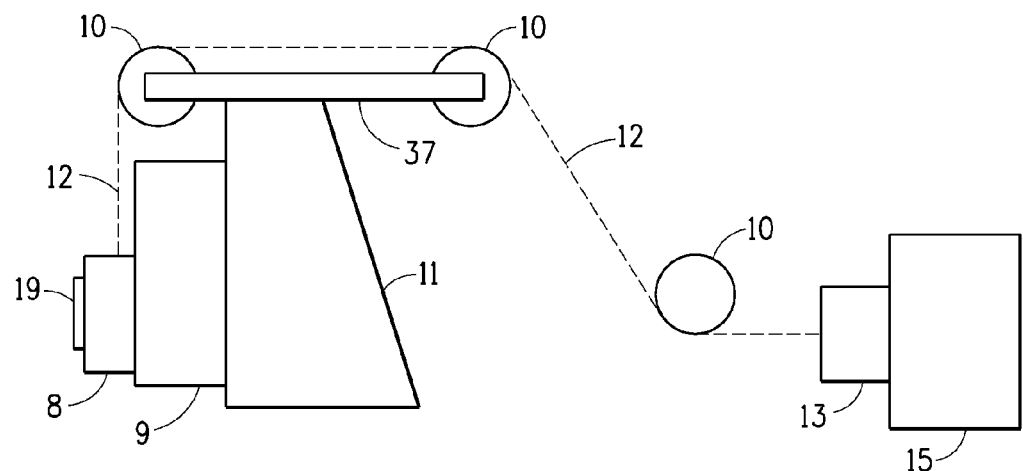
FIG. 2 is a side view of the blade holder and related support.

Operation of the equipment shown in FIGS. 1 and 2 involves the following sequence of steps. The test specimens are cut from a sheet of material to be tested. The specimens can be cut using a variety of methods including die cutting and water jet cutting. The test specimen is then mounted in the mechanical grips 1. Care should be taken to assure the specimen gauge length is the same for each test. This can be accomplished by carefully measuring the distance between the specimen grips or creating a jig to hold the grips while mounting the specimen.

Once the specimen is mounted, the grips are attached to the load cells 4 and 22. With the blade installed and the test specimen in place, the test is ready to begin. The desired test specimen tension is selected using the PC controller. The tension setting will vary for different materials and specimen thicknesses. A typical tension setting for an elastomeric material specimen is between 200 and 2000 grams. Next, the desired horizontal cutting block load is set using the PC controller. A setting of between the 200 and 5000 grams is typical of most materials likely to be tested. With the desired test specimen tension and horizontal cutting block load selected the test is ready to begin.

The test sequence is as follows. The PC controller directs the actuator 15 attached to the blade holder to lower the blade into the starting position. The hydraulic actuators 14 attached to the test specimen begin to retract thus increasing the specimen tension. These actuators continue to move until the desired test specimen tension is achieved. The PC controller will switch to a load control mode and continue to maintain this level of tension until the testing is complete.

With the appropriate level of tension applied to the test specimen the equipment is ready to begin pressing the test specimen 7 against the blade 19 with the cutting block 5. The PC controller will slowly extend the actuator 17 with the cutting block 5 towards the test specimen 7. As the cutting block moves forward, the horizontal groove 28 in the block slides over the test specimen capturing the specimen and holding it in position for cutting. The actuator continues to move forward until the exposed blade edge passes through the vertical groove 29 in the cutting block. Finally, the actuator will press the test specimen against the blade 19. The cutting block will continue to slowly move—pressing the test specimen against the blade until the desired horizontal cutting block load is reached. The PC controller will switch into a load control mode and maintain this level of compression until the testing is complete.

Once the appropriate tensile and compressive loadings are applied to the test specimen, the PC controller will begin retracting the actuator 15 which moves the blade holder 8 and the blade 19. As the actuator moves, the blade 19 is pulled vertically across the specimen 7. The rate at which the blade 19 moves is controlled by the PC controller. A typical setting for an elastomeric material such as tire rubber is 6.35 mm/sec. The actuator will continue to travel until the specimen is cut or the entire blade has traversed the specimen without cutting the specimen. Cut-through occurs when the test specimen tension drops to zero or the cutting block comes in contact with the blade. If the specimen is not cut, the load at which the test specimen is pressed against the blade should be increased and the test re-run using a new test specimen. Following the test sequence, all actuators are returned to their starting positions to allow the equipment to be prepared for another test specimen. During the test sequence, the PC controller or an independent data acquisition system monitors and records all actuator movement via displacement transducers and actuator loads with load cells.

The test is repeated as required to provide appropriate statistical data. A typical test would generally involve at least five specimens, each having different horizontal cutting block pressure loadings. For a given horizontal load on the cutting block, a more cut resistant material would require greater blade travel.

It is clear to the skilled artisan that mechanical equivalents to the above-described apparatus means could also be used in this invention. For example, rather than using hydraulic actuators to control the application of test specimen tension or load which the test specimen is pressed against the blade, one could use linear motors or pneumatic actuators. Similarly, the mechanical grips used to hold the test specimen could be replaced with pneumatic grips to facilitate specimen installation.

The invention claimed is:

1. An apparatus comprising
  (a) first and second specimen holding and tensioning devices arranged on a common axis wherein the tensioning devices each comprise an assembly of components connected together in the sequential order of specimen grip, connecting rod, release coupling, load cell and an actuator,
  (b) a blade cutting device located orthogonally to the axis of the first and second specimen tensioning devices wherein the cutting device further comprises a cutting blade, a blade holder on a linear slide attached to a backing plate, a load cell wherein the blade holder is connected to the load cell and actuator via a wire mounted over a plurality of pulleys, and (c) a cutting block assembly located on the same axis as the cutting device and on the opposite side of the specimen tensioning device axis wherein the block assembly comprises a series of components connected together in the sequential order of cutting block, air cylinder, load cell and actuator wherein the cutting block further comprises a first slot cut horizontally across the block to locate the test specimen and a second slot cut vertically to locate the cutting blade.

2. A method for determining the cut resistance of flexible sheet materials comprising the steps of (a) positioning a test specimen between the grips of first and second holding and tensioning devices, (b) applying and maintaining tension to the test specimen by means of actuators on the first and second tensioning devices, (c) aligning a cutting block that has a slot cut horizontally across the block and a second slot cut vertically located orthogonally to the test specimen such that the test specimen rests against the face of the horizontal slot cut into the cutting block, (d) positioning a blade cutting device located on the same axis as the cutting block assembly, but on the opposite side of the specimen tensioning device axis such that the blade fits into the vertical slot cut into the cutting block and that the top of the blade makes contact with the test specimen, (e) moving the blade upwards in a vertical direction across the specimen until the test is ended by means of an actuator and connecting wire of the cutting device while applying pressure on the test specimen from an actuator of the cutting device so as to cut simultaneously across the entire width of the test specimen through the thickness of the specimen as the blade is in travel, (f) analyzing data collected during the test to determine cut resistance.

\* \* \* \* \*